United States Patent [19]

Hill et al.

[11] Patent Number: 4,892,820

[45] Date of Patent: Jan. 9, 1990

[54] SOLVENT SYSTEM FOR ENZYMATIC COUPLING PROCESS

[75] Inventors: John B. Hill, Woodstock; Steven O. Roczniak, Chicago, both of Ill.

[73] Assignee: The Nutrasweet Company, Deerfield, Ill.

[21] Appl. No.: 60,286

[22] Filed: Jun. 10, 1987

[51] Int. Cl.$^4$ .................... C12P 21/02; C12P 21/04
[52] U.S. Cl. ..................... 435/68.1; 560/40
[58] Field of Search ............ 435/106, 70, 71, 68; 560/40

[56] References Cited

U.S. PATENT DOCUMENTS

| | | | |
|---|---|---|---|
| 4,284,721 | 8/1981 | Nehimura et al. | 435/70 |
| 4,371,464 | 2/1983 | Boesten et al. | 560/40 |
| 4,634,790 | 1/1987 | Shinohara et al. | 560/40 |
| 4,677,220 | 6/1987 | Tou et al. | 560/40 |
| 4,684,745 | 8/1987 | Takemoto et al. | 560/40 |
| 4,710,583 | 12/1987 | Chmurny et al. | 435/70 |
| 4,760,164 | 7/1988 | Park et al. | 560/40 |
| 4,801,732 | 1/1989 | Mita et al. | 564/40 |
| 4,806,473 | 2/1989 | Johansen et al. | 435/70 |
| 4,810,817 | 3/1989 | Chmurny et al. | 560/40 |

*Primary Examiner*—Herbert J. Lilling
*Attorney, Agent, or Firm*—John M. Sanders

[57] ABSTRACT

Alkylphosphate solvents are disclosed for use in an amino acid and amino acid ester enzymatic coupling process. α-Aspartylphenylalanine methyl ester and intermediates thereof are prepared enzymatically in an alkylphosphate solvent or cosolvent.

20 Claims, No Drawings

SOLVENT SYSTEM FOR ENZYMATIC COUPLING PROCESS

BACKGROUND OF INVENTION

The present invention relates to an improved solvent system for enzymatic coupling processes. In particular, alkylphosphates are employed as a solvent or cosolvent in the enzymatic coupling of amino acids and/or amino acid esters.

The enzymatic coupling of amino acids to form dipeptides and tripeptides has received a lot of attention in recent years due to the increasing commercial utility of these compounds and their relatively high costs of production by chemical processing. Aspartame, a dipeptide, can be made by a variety of chemical processes which are relatively expensive. A more efficient way to produce aspartame (APM) is to enzymatically couple its two amino acid components; i.e., aspartic acid and phenylalanine (Phe) or Phe methyl ester. However, problems are associated with this enzymatic coupling reaction including solubility, recovery and recycling problems. Additionally, many solvent systems are incompatible with enzymes employed in these reactions.

The present invention provides an improved solvent system for enzymatic coupling processes. The improved solvent system is cheap, provides desirable solubility characteristics and allows for easy recovery of solvent. The solvent system can also be easily recycled.

SUMMARY OF INVENTION

Briefly, in accordance with the present invention, amino acids and/or amino acid esters are enzymatically coupled in an alkylphosphate solvent system. The alkylphosphate can be the sole solvent or a cosolvent in a multiple solvent system.

Of particular interest in the practice of the present invention, triethylphosphate is employed as the sole solvent or as a cosolvent with (a) water or (b) isooctane and a minor portion of water in an enzymatic coupling process to produce aspartame ($\alpha$-L-aspartyl-L-phenylalanine methyl ester (APM)) or an aspartame intermediate such as $\alpha$-L-aspartyl-L-phenylalanine (AP), $\alpha$-L-aspartyl-L-phenylalanine dimethyl ester (MAPM) or $\alpha$-L-aspartyl-$\beta$-methyl ester-phenylalanine (MAP).

DETAILED DESCRIPTION OF THE INVENTION

In practicing the present invention, an alkylphosphate or mixtures of alkylphosphates are employed as the solvent or cosolvent in an enzymatic coupling process wherein two amino acids or derivatives thereof are coupled to form a dipeptide or dipeptide derivative. The alkylphosphates correspond to the formula:

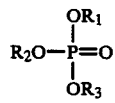

wherein $R_1$, $R_2$ and $R_3$ each independently represent H or $C_1$–$C_8$ alkyl, any of $R_1$, $R_2$ and $R_3$ may combine to form a ring structure having from 2-4 carbon atoms, and the proviso that at least one of $R_1$, $R_2$ and $R_3$ must be a $C_1$–$C_8$ alkyl.

The alkylphosphate solvents are known compounds. A preferred solvent is triethylphosphate which is commercially available.

The particular amino acids or amino acid derivatives coupled in the present process are not critical. The amino acids can be any of the naturally occuring or synthetic amino acids. Derivatives of amino acids including their salts and esters as well as dipeptides are also coupled in the present process. Preferred amino acids include L-aspartic acid (L-Asp) and L-phenylalanine (L-Phe), the two amino acids coupled to form aspartame or intermediates of aspartame. Preferred derivatives of these two amino acids include the methyl esters of both, i.e. L-phenylalanine methyl ester (L-PM), $\alpha$- and $\beta$-L-aspartic acid methyl ester ($\alpha$-L-AspOMe and $\beta$-L-AspOMe) and L-aspartic acid dimethyl ester [L-Asp(OMe)$_2$]

The particular enzymes employed to couple the amino acids or amino acid derivatives according to the present process are not critical. Any enzyme capable of coupling the desired amino acids and/or derivatives is acceptable. Mixtures of enzymes can also be employed. Suitable enzymes are those which effect the aminolysis of amino acid esters by amino acids and their esters to yield peptides. Specific enzymes include (1) peptidase E. described by Carter et al.. Journal of Bacteriology, 159 (2), 453–459 (1984); (2) leucine aminopeptidase from pig kidney (E.C. 3.4.11.1); (3) alpha-aminoacylpeptide hydrolases; (4) peptidase E from *Salmonella typhimurium* TN 1246 and (5) dipeptide hydrolases.

The temperature and pressure at which the present coupling process is conducted is not critical. Advantageously, ambient temperature and pressure conditions are employed. The order of mixing the reactants, enzymes and solvent or cosolvents is not critical either. Usually, if water is employed as a cosolvent, the enzymes are added to the water and then this aqueous phase is mixed with the amino acids and/or derivatives, the alkylphosphate cosolvent and any other cosolvents optionally employed. Preferably the amino acids or derivatives are mixed with the alkylphosphate solvent and any other optional organic solvent prior to mixture with an aqueous phase.

The present invention includes the use of alkyphosphates as the sole solvent in an enzymatic coupling process. However, a cosolvent reaction medium is preferably employed. Solvents employed in addition to the alkylphosphate include water and non-polar hydrocarbons such as hexane, isooctane and the like. The optimum solvent system will depend on a variety of factors, such as, for example, the particular starting materials and their solubilities, the particular enzyme employed and the resulting end product which is formed. One skilled in the art can readily determine an optimal solvent system by conducting routine experiments.

When a cosolvent reaction medium is employed, the alkylphosphate will usually be present in amounts of from about 2 to about 95 percent by weight of the reaction medium and preferably from about 8 to about 60 percent by weight.

In one embodiment of the present invention, $\alpha$-L-aspartic acid methyl ester ($\alpha$-AM) and L-phenylalanine methyl ester (PM) are reacted in the presence of an enzyme employing water and triethylphosphate (TEP) as a cosolvent system wherein the TEP/water ratio is from about 1:10 to 10:1. TEP and water are miscible and PM is soluble in this cosolvent system. The reaction is conducted and at its conclusion the TEP is extracted with an organic solvent, such as xylene or toluene. The resulting aqueous phase has the end product α-L-aspartyl-L-phenylalanine methyl ester (aspartame) which is recovered employing standard recovery techniques.

In another embodiment, at least about 8 percent by weight of the reaction mixture is comprised of TEP as a cosolvent in combination with a non polar organic solvent such as hexane or isooctane and a minor amount of water, i.e. 0.5-5% by weight. When minor amounts of water are employed, a surfactant is added to the reaction mixture in an amount effective to produce a reverse micellar system which maintains enzymatic activity. With this reaction medium, it is preferred to employ L-aspartic acid dimethyl ester (MAM) and PM as the amino acid ester starting materials which results in the formation of the dimethyl ester of aspartame (MAPM). The MAPM is soluble in the organic phase of the reaction mixture and is recovered employing standard techniques. The MAPM can then be de-esterified into APM employing standard de-esterification techniques.

In another embodiment, water and TEP are employed as cosolvents in the reaction of the dimethyl or α-methyl esters of aspartic acid with L-Phe resulting in the formation of a-L-aspartyl-L-phenylalanine (a-AP) or a-L-aspartyl methyl ester-L-phenylalanine (a-MAP). After the reaction is complete, the TEP is extracted with a non-polar organic solvent. The a-AP or a-MAP remains in the aqueous phase and can be readily processed into APM.

The following examples illustrate the practice of the present invention, but should not be construed as limiting its scope.

EXAMPLE 1

Retention Of Enzyme Activity

A reverse micellar solution containing isooctane/0.1M aerosol-OT surfactant and leucine aminopeptidase in 50mM potassium phosphate at a pH of 7.2 was prepared. The water/aerosol-OT molar ratio was 15. TEP was added to this solution to a final amount of 10% v/v resulting in the formation of two layers. The retention of enzymatic activity was confirmed by demonstrating the hydrolysis of L-leucine-p-nitroanilide which is the classical substrate for this enzyme. Hydrolysis of the substrate was confirmed by a yellow color forming in the lower layer.

In similar operations the various amino acids and/or derivatives are coupled with an appropriate enzyme employing an alkyl phosphate, i.e., TEP, as the sole solvent or as a cosolvent with water and/or non-polar organic solvents.

EXAMPLE 2

Retention of Enzyme Activity 36 microliters (ml) of the enzyme leucine aminopeptidase (LAP) solution (LAP dissolved in 50 mM potassium phosphate, pH 7.2 to give an activity 1 unit/ml) and 18 microliters of the substrate L-leucine p-nitroanilide (LeupNAHCl) solution (LeupNA dissolved in 50 mM potassium phosphate, PH6.0, to give a concentration of 250 mM) were added to 2ml isooctane containing 0.1M aerosol-OT (AOT) surfactant. Ten (10) percent by volume triethylphosphate (TEP) was added to the above solutions. The resulting assay mixture was shaken at 200 rpm for 2 days at room temperature. Two layers developed in the assay mixture. The bottom layer contained the yellow p-nitroaniline product which indicates that the enzyme retained activity in the presence of 10% v/v TEP.

EXAMPLE 3

Solubility of L-PM and MAPM

A 10% v/v TEP/isooctane/0.1M AOT reaction mixture dissolved L-PM and MAPM free bases in amounts of 20 mg/ml. 1, 3 and 5% TEP/isooctane/0.1M AOT reaction mixtures did not dissolve L-PM and MAPM free bases in amounts of 20 mg/ml.

We claim:

1. In an enzymatic coupling process for coupling amino acids and/or amino acid esters and derivatives, the improvement which comprises:
   an alkylphosphate as a solvent or cosolvent.

2. The improved process of claim 1 wherein the alkylphosphate is triethylphosphate.

3. The improved process of claim 2 wherein triethylphosphate is a cosolvent in combination with a non-polar organic solvent and a minor amount of water.

4. The improved process of claim 2 wherein the triethylphosphate is a cosolvent in combination with water.

5. The improved process of claim 1 wherein the amino acids and/or esters thereof are coupled to form aspartame, a-L-aspartyl-L-phenylalanine, a-L-aspartyl-L-phenylalanine dimethyl ester or a-L-aspartyl-β-methyl ester-L-phenylalanine.

6. The improved process of claim 5 wherein the alkylphosphate is triethylphosphate.

7. The improved process of claim 6 wherein the triethylphosphate is a cosolvent in combination with a non-polar organic solvent and a minor amount of water.

8. The improved process of claim 6 wherein the triethylphosphate is a cosolvent in combination with water.

9. An enzymatic process for coupling amino acids and/or amino acid esters which comprises:
   (a) contacting a first amino acid or ester thereof with a second amino acid or an ester thereof in the presence of
       (i) an effective coupling amount of an enzyme and
       (ii) an alkylphosphate as the sole solvent or as a cosolvent in a multi-solvent system.

10. The enzymatic process of claim 9 wherein the alkylphosphate is a compound or a mixture of compounds corresponding to the formula:

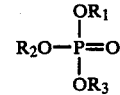

wherein $R_1$, $R_2$ and $R_3$ each independently represent H or a $C_1$-$C_8$ alkyl,
   any of $R_1$, $R_2$ or $R_3$ may combine to form a ring structure having from 2-4 carbon atoms,
   with the proviso that at least one of $R_1$, $R_2$ and $R_3$ must be a $C_1$-$C_8$ alkyl.

11. The enzymatic process of claim 10 wherein the alkylphosphate is triethylphosphate.

12. The enzymatic process of claim 11 wherein the first amino acid or ester thereof is aspartic acid, aspartic acid-a-methylester or aspartic acid dimethyl ester and the second amino acid or ester thereof is phenylalanine or phenylalanine methyl ester.

13. The enzymatic process of claim 12 wherein the triethylphosphate is a cosolvent in combination with a non-polar organic solvent and a minor portion of water.

14. The enzymatic process of claim 12 wherein the triethylphosphate is a cosolvent in combination with water.

15. In an enzymatic process for preparing aspartame, a-L-aspartyl-L-phenylalanine dimethyl ester, a-L-aspartyl-β-methyl ester-L-phenylalanine or a-L-aspartyl-L-phenylalanine by coupling (a) aspartic acid or an appropriate methyl ester thereof with (b) phenylalnine or phenylalanine methyl ester in the presence of a solvent and an effective amount of an enzyme, the improvement which comprises:

an alkylphosphate as the solvent or cosolvent

16. The improved enzymatic process of claim 15 wherein the alkylphosphate is triethylphosphate.

17. The improved enzymatic process of claim 16 wherein the triethylphosphate is a cosolvent with a non-polar organic solvent and a minor amount of water.

18. The improved process of claim 17 wherein the non-polar solvent is a hydrocarbon.

19. The improved process of claim 18 wherein the non-polar hydrocarbon solvent is octane, hexane or isooctane.

20. The improved process of claim 16 wherein the triethylphosphate is a cosolvent in combination with water.

* * * * *